United States Patent [19]

Padron

[11] Patent Number: 5,155,213

[45] Date of Patent: Oct. 13, 1992

[54] METHOD FOR ISOLATING IGAS IN THE FECES

[76] Inventor: Eloy Padron, 235 SW. Le Jeune Rd., Miami, Fla. 33134

[21] Appl. No.: 783,198

[22] Filed: Oct. 28, 1991

[51] Int. Cl.⁵ .......................................... A61K 39/395
[52] U.S. Cl. ................................. 530/387.1; 530/861
[58] Field of Search ........................................ 530/387

[56] References Cited

PUBLICATIONS

Seminar sponsored by American College of Allergy & Immulogy, (47th Annual Meeting), Lectures: Postley, M.D. & Eindbinder, PhD on Nov. of 1990 in San Francisco, Calif.

*Primary Examiner*—Howard E. Schain
*Attorney, Agent, or Firm*—Jesus Sanchelina

[57] ABSTRACT

A method for isolating the IgAs in the feces of animals and humans including the steps of placing said feces in a container with a buffer solution, homogenizing the feces in a phosphate buffer saline solution thereby forming a homogenized solution, separating the solids from the homogenized solution leaving a clear solution and chemically precipitating substantially all material contained in the clear solution with the exception of the IgAs through the use of protamine. The method produces a sufficient amount of IgAs for diagnostic and treatment purposes, if necessary.

8 Claims, No Drawings

METHOD FOR ISOLATING IGAS IN THE FECES

BACKGROUND OF THE INVENTION

1. Field of the Invention

The present invention relates to a method for isolating the IgAs in human and animal feces, and more particularly, to such method that is used in the diagnosis and treatment of allergies and diseases associated with deficiencies in the immulogical system of patients.

2. Description of the Related Art

Applicant believes that the closest reference corresponds to a seminar that took place in San Francisco and sponsored by the American College of Allergy & Immulogy (47th Annual Meeting) in November of 1990 (lecturers: J. E. Postley, M.D. and J. Einbinder, PhD) wherein it was discussed that IgAs can be obtained from the saliva to make certain determinations concerning the presence of antigens/antibodies. The method disclosed, however, required the production of approximately 30 cc of saliva from a patient in order to obtain IgAs in the micro-grams range. The unreliability of using any conventional diagnosis method from these minimal quantities of IgAs is quite apparent. Also, the undesirability of the method from the patient's standpoint is obvious.

To determine the presence of antigens and/or antibodies many conventional methods have been used in the past. Most of them, using an enzyme conjugated with another chemical substance to detect the presence, and with some methods, approximate the quantity of the antigens and antibodies. Typically, these methods are used in conjunction with blood drawn from the patient and the immunoglobin classes tested are the IgE and IgG4. However, IgAs is not present in the blood drawn from an individual in appreciable quantities since it is mainly created by the mucous, such as the intestines' mucous membranes, and being eventually stored in the feces. The information carried in general immunity IgE and IgG4 is not as relevant as the one included in the local immunity IgAs. The conventional methods include those that use conjugated enzymes, such as, ELISA, RIA, radio immuno assay, immunofluorescent methods, dots/disks, strips methods, etc. None of these methods are directed towards the use of IgAs since it is not present in the blood drawn from the patient in appreciable quantities.

SUMMARY OF THE INVENTION

It is one of the main objects of the present invention to provide a method for detecting, identifying qualitatively and quantitatively the presence of antigens and antibodies in a person or animal.

It is another object of this invention to provide a method that is reliable and does not present inconveniences to the user.

It is still another object of the present invention to provide a method that can be readily used.

It is yet another object of this invention to provide such a method that is inexpensive to utilize.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The preferred manner of practicing the present invention will be described below. The inventor has obtained excellent results, compared to the other conventional methods. The first step is to obtain the feces, human or animal, and place them in a container with a buffer solution. This buffer solution can be implemented with the use of a water base solution that includes a phosphate and sodium chloride, such as conventionally known PBS (phosphate buffer saline) solution. Preferably, a 0.010 molar solution is used with a pH of 7.6. In the preferred manner contemplated by the inventor, 10% of the weight will be the feces and the remaining 90% will be the buffer solution. This is not critical and in practive the buffer solution is estimated by volume and the feces by weight, equating the densities of the feces and the buffer solution. Also, merthiolate (0.1% concentration) is added to kill any bacteria and to minimize the odor of the feces.

The second step involves the homogenization of the feces in the buffer solution and this is accomplished with an homogenizer rotating its blades at 28,000 R.P.M. in the preferred embodiment. This is done for approximately 5 minutes. The resulting liquid is typically brown and the lympho cells are destroyed.

Then, the homogenizer is stopped for 5 minutes and after that it is started again for another 5 minutes. Again, it is stopped once more and started once again for the final 5 minutes. After that, the liquid is centrifuged to separate the solids from the liquid and depending on the particular constitution of the feces (fiber content, etc.) sufficient time is allowed for the liquid to clear.

The next step is to add protamine (at 1% concentration, a fish extract typically) so that everything precipitates except the IgAs which remains either in solution (conjugated with the protamine) or in suspension. In the preferred case, about 1 mg. in 1% concentration is added to about 6 or 7 cc of the clear liquid after decanting. In a typical case, the inventor herein has been able to obtain samples in the order of hundreds of milligram of IgAs which is enough for an accurate analysis using the conventional enzyme methods described above (ELISA, RIA, etc.).

The production of IgAs in sufficient quantities makes it possible not only to properly diagnose the patients' immulogical deficiencies but also to produce IgAs in sufficiently large quantities to administer it conjugated with the pertinent allergens to rebuild the patients' immunity.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for isolating IgAs in the feces of animals and humans including the steps of:
   A. placing said feces in a container with a buffer solution;
   B. homogenizing the feces in said buffer solution thereby forming a homogenized solution;
   C. separating the solids from said homogenized solution leaving a clear solution; and D. chemically precipitating substantially all material contained in said clear solution with the exception of the IgAs through the use of protamine.

2. The method set forth in claim 1 further including the step of:

E. using a method for the detection and classification of antigens and antibodies found in said isolated IgAs.

3. The method set forth in claim 1 wherein said buffer solution includes an effective amount of a bacteria suppressing substance.

4. The method set forth in claim 3 wherein said bacteria suppressing substance includes a merthiolate solution.

5. The method set forth in claim 4 wherein in said homogenized solution substantially all lymph cells have been destroyed.

6. The method set forth in claim 5 wherein said homogenizing step is performed twice and having a rest period in between.

7. The method set forth in claim 6 wherein said buffer solution includes a phosphate buffer saline solution.

8. The method set forth in claim 7 wherein said homogenization is performed with a homogenizer with blades that rotate at a speed in excess of 20,000 revolutions per minute.

* * * * *